(12) United States Patent
Yamae et al.

(10) Patent No.: US 10,162,170 B2
(45) Date of Patent: Dec. 25, 2018

(54) OPTICAL DEVICE

(71) Applicant: PANASONIC INTELLECTUAL PROPERTY MANAGEMENT CO., LTD., Osaka (JP)

(72) Inventors: Kazuyuki Yamae, Nara (JP); Shintaro Hayashi, Hyogo (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 0 days.

(21) Appl. No.: 15/659,766

(22) Filed: Jul. 26, 2017

(65) Prior Publication Data
US 2018/0039063 A1    Feb. 8, 2018

(30) Foreign Application Priority Data
Aug. 3, 2016   (JP) .................. 2016-153248

(51) Int. Cl.
| F21V 7/04 | (2006.01) |
| G01S 1/00 | (2006.01) |
| G09B 9/00 | (2006.01) |
| H01S 3/00 | (2006.01) |
| H01S 3/30 | (2006.01) |
| G02B 23/24 | (2006.01) |

(Continued)

(52) U.S. Cl.
CPC ........ *G02B 23/2469* (2013.01); *A61B 1/0653* (2013.01); *F21V 9/30* (2018.02); *G02B 19/0009* (2013.01); *G02B 19/0052* (2013.01); *G02B 23/2453* (2013.01); *G02B 23/2476* (2013.01); *G02B 27/0916* (2013.01); *F21Y 2115/30* (2016.08)

(58) Field of Classification Search
USPC .............. 385/88, 93; 362/553; 235/454, 455
See application file for complete search history.

(56) References Cited

U.S. PATENT DOCUMENTS

| 7,733,310 B2 * | 6/2010 | Hajjar ................ B82Y 10/00 345/84 |
| 8,716,736 B2 | 5/2014 | Yamae et al. |

(Continued)

FOREIGN PATENT DOCUMENTS

| JP | 2000-275444 A | 10/2000 |
| JP | 2004-253783 A | 9/2004 |

(Continued)

*Primary Examiner* — Tuyen K Vo
(74) *Attorney, Agent, or Firm* — Greenblum & Bernstein, P.L.C.

(57) ABSTRACT

An optical device includes: an excitation light source; a first light transmitter that transmits excitation light emitted from the excitation light source; a fluorescent light part that is disposed on a surface of the first light transmitter opposite a surface through which the excitation light enters, and emits fluorescent light from the excitation light; a second light transmitter that interposes the fluorescent light part with the first light transmitter, and transmits light emitted from the fluorescent light part; a light transmission fiber that guides the light exiting from the second light transmitter; and a microfabricated film that is disposed on a side of the second light transmitter closer to the light transmission fiber, and collects, toward the light transmission fiber, the light emitted from the fluorescent light part.

5 Claims, 6 Drawing Sheets

(51) Int. Cl.
   *F21V 9/30*      (2018.01)
   *G02B 19/00*     (2006.01)
   *A61B 1/06*      (2006.01)
   *G02B 27/09*     (2006.01)
   *F21Y 115/30*    (2016.01)

(56) References Cited

U.S. PATENT DOCUMENTS

| | | | |
|---|---|---|---|
| 9,112,181 B2 | 8/2015 | Yamae et al. | |
| 9,753,275 B2 | 9/2017 | Motoya et al. | |
| 2003/0229270 A1* | 12/2003 | Suzuki | A61B 1/043 600/178 |
| 2006/0018609 A1 | 1/2006 | Sonoda et al. | |
| 2006/0034571 A1 | 2/2006 | Nagano et al. | |
| 2010/0140640 A1* | 6/2010 | Shimokawa | H01L 33/0079 257/98 |
| 2010/0157036 A1* | 6/2010 | Sugimoto | A61B 1/00009 348/65 |
| 2014/0022810 A1 | 1/2014 | Ito et al. | |
| 2014/0104689 A1* | 4/2014 | Padiyath | G02B 5/0242 359/592 |
| 2014/0221794 A1* | 8/2014 | Yamaguchi | A61B 1/00009 600/322 |
| 2014/0225099 A1 | 8/2014 | Yamae et al. | |
| 2015/0034929 A1 | 2/2015 | Ide et al. | |
| 2015/0041783 A1 | 2/2015 | Ide et al. | |
| 2015/0069349 A1 | 3/2015 | Hayashi et al. | |
| 2015/0286120 A1* | 10/2015 | Ohno | G02B 26/101 353/84 |
| 2016/0054558 A1 | 2/2016 | Ito et al. | |

FOREIGN PATENT DOCUMENTS

| | | |
|---|---|---|
| JP | 2006-054366 A | 2/2006 |
| JP | 2006-066875 A | 3/2006 |
| JP | 2012-209190 A | 10/2012 |
| JP | 2015-210872 A | 11/2015 |
| JP | 2016-034505 A | 3/2016 |
| JP | 2016-092042 A | 5/2016 |
| WO | 2012/133632 A1 | 10/2012 |

* cited by examiner

OPTICAL DEVICE

CROSS REFERENCE TO RELATED APPLICATION

This application claims the benefit of priority of Japanese Patent Application Number 2016-153248 filed on Aug. 3, 2016, the entire content of which is hereby incorporated by reference.

BACKGROUND

1. Technical Field

The present disclosure relates to an optical device used in endoscopes, for example.

2. Description of the Related Art

Conventionally, a laser module including: a semiconductor laser element; a collecting lens that collects laser beams from the semiconductor laser element; and an optical fiber held at a position of laser beam convergence by the collecting lens is disclosed (see Japanese Unexamined Patent Application Publication No. 2006-66875 (Patent Literature (PTL) 1), for example).

A light source system including a phosphor is also disclosed (see Japanese Unexamined Patent Application Publication No. 2012-209190 (PTL 2), for example).

SUMMARY

However, there is a demand to increase the density of light bundles collected by the light guide, by enhancing dissipation of heat from the fluorescent light part and collection of light toward the light guide as compared to the optical devices disclosed in PTL 1 and PTL 2.

In view of this, the present disclosure has an object to provide an optical device capable of enhancing dissipation of heat from a fluorescent light part and collection of light toward a light guide.

In order to achieve the above object, an optical device according to an aspect of the present disclosure is an optical device including: an excitation light source; a first light transmitter that transmits excitation light emitted from the excitation light source; a fluorescent light part that is disposed on a surface of the first light transmitter opposite a surface through which the excitation light enters, and emits fluorescent light from the excitation light; a second light transmitter that interposes the fluorescent light part with the first light transmitter, and transmits light emitted from the fluorescent light part; a light guide that guides the light exiting from the second light transmitter; and a light collecting structure that is disposed on a side of the second light transmitter closer to the light guide, and collects, toward the light guide, the light emitted from the fluorescent light part.

According to the present disclosure, it is possible to enhance dissipation of heat from a fluorescent light part and collection of light toward a light guide.

BRIEF DESCRIPTION OF DRAWINGS

The figures depict one or more implementations in accordance with the present teaching, by way of examples only, not by way of limitations. In the figures, like reference numerals refer to the same or similar elements.

DETAILED DESCRIPTION OF EMBODIMENT

Figure 1:
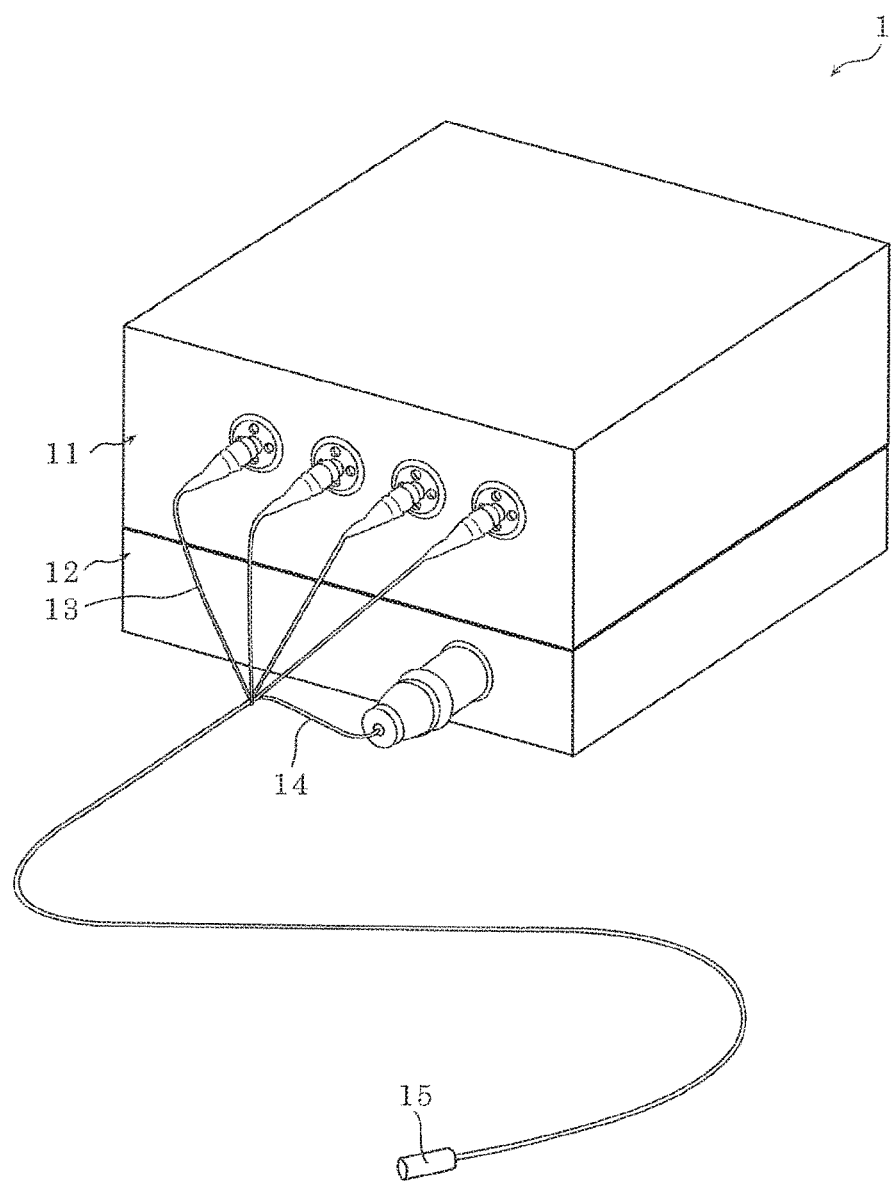
FIG. 1 is a perspective view illustrating an optical device according to an embodiment.

Hereinafter, an embodiment will be described with reference to the drawings. Note that the embodiment described below presents a general or specific example. The numerical values, shapes, materials, elements, the arrangement and connection of the elements, steps, and the processing order of the steps, etc. presented in the following embodiment are examples and do not limit the present disclosure. Further, among the elements in the following embodiment, elements not recited in any one of the independent claims which indicate the broadest inventive concepts are described as arbitrary elements.

Furthermore, the term "approximately . . . " is intended to encompass, in an example case of "approximately identical", not only what is exactly identical but also what can be recognized as substantially identical.

Note that the figures are schematic diagrams and are not necessarily precise illustrations. Additionally, elements that are essentially the same share like reference numerals in the figures, and overlapping explanations thereof are omitted or simplified.

(Embodiment)
[Configuration]

First, the configuration of optical device 1 according to the present embodiment will be described with reference to FIG. 1 to FIG. 3.

FIG. 1 is a perspective view illustrating optical device 1 according to the present embodiment. FIG. 2 is a block diagram illustrating optical device 1 according to the present embodiment. FIG. 3 is a schematic cross sectional view illustrating, for example, excitation light source 2, first light transmitter 3, and second light transmitter 5 of optical device 1 according to the present embodiment.

Figure 3:
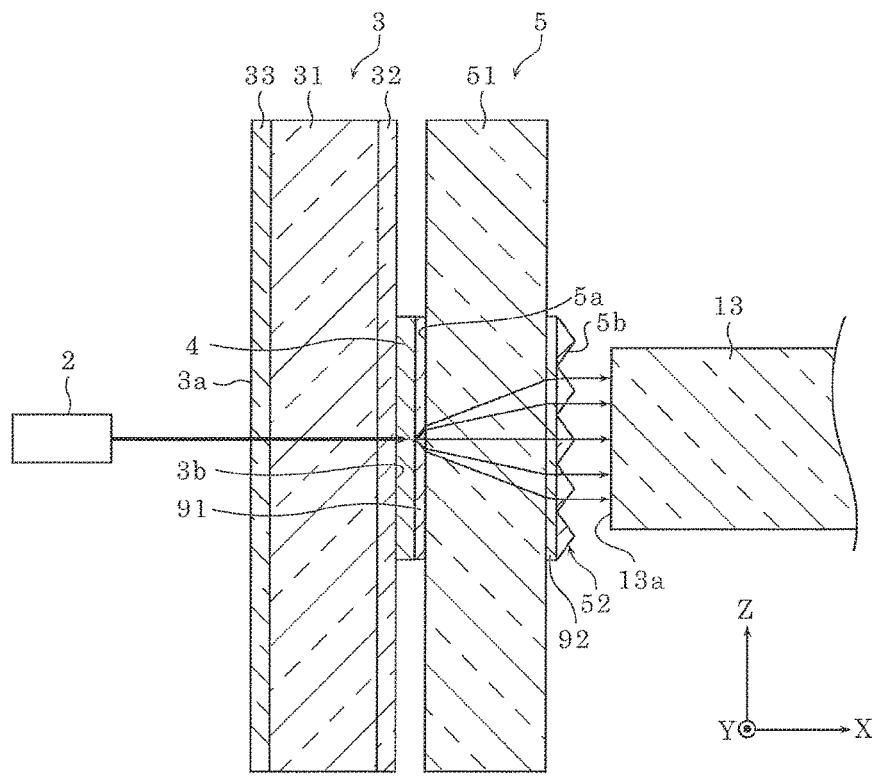
FIG. 3 is a schematic cross sectional view illustrating, for example, an excitation light source, a first light transmitter, and a second light transmitter of the optical device according to the embodiment.

FIG. 3 shows X direction, Y direction, and Z direction where X positive direction is the direction of the optical axis of excitation light source 2, Z positive direction is the direction perpendicular to the X positive direction, and Y positive direction is the direction perpendicular to the X positive direction and the Z positive direction. The directions shown in FIG. 3 correspond to directions shown in FIG. 4. Note that the X direction, the Y direction, and the Z direction are not limited to those shown in FIG. 3 because they change depending on usage. The same applies to the subsequent figures.

As illustrated in FIG. 1, optical device 1 according to the present embodiment is used in an endoscope, for example, and includes laser light unit 11, camera control unit 12, light transmission fiber 13, image transmission path 14, and Lip end portion 15.

One side of light transmission fiber 13 is connected to laser light unit 11. One side of image transmission path 14 is connected to camera control unit 12. The other side (tip) of light transmission fiber 13 and image transmission path 14 is tip end portion 15. Portions of light transmission fiber 13, image transmission path 14, and tip end portion 15 that are passed into a body are called an endoscope.

Figure 2:
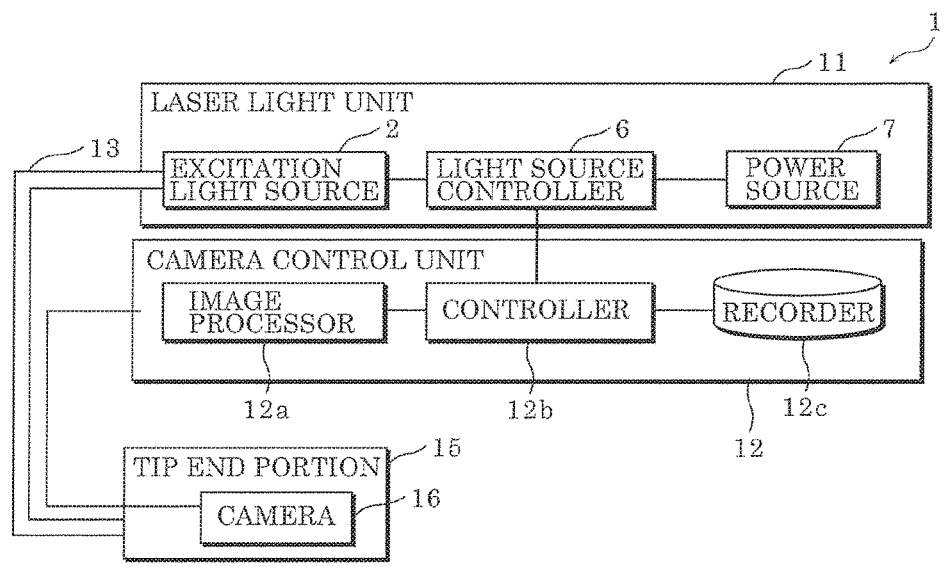
FIG. 2 is a block diagram illustrating the optical device according to the embodiment.

As illustrated in FIG. 2 and FIG. 3, laser light unit 11 includes excitation light source 2, first light transmitter 3, fluorescent light part 4, second light transmitter 5, light transmission fiber 13 (an example of a light guide), light source controller 6, and power source 7. Excitation light source 2, first light transmitter 3, fluorescent light part 4, second light transmitter 5, light source controller 6, and power source 7, for example, are accommodated in a housing of laser light unit 11.

Excitation light source 2 irradiates a predetermined position in first light transmitter 3 with excitation light. Excitation light excites a phosphor in fluorescent light part 4 so as to cause the phosphor to emit fluorescent light. Specifically, excitation light source 2 is disposed in the housing in such a manner that the optical axis of excitation light source 2 is approximately perpendicular to first light transmitter 3. Excitation light source 2 can be formed with a semiconductor laser that emits excitation light in a range (waveband) from ultraviolet light, which is shorter in wavelength than blue excitation light, to blue light, for example. An indium gallium nitride (InGaN) laser diode or an aluminum indium gallium nitride (AlInGaN) laser diode, for example, can also be used as excitation light source 2. Accordingly, the excitation light in the present embodiment may be laser light. For example, blue excitation light does not mean blue light in a strict sense but it means light in a waveband that usually appears blue.

Note that the excitation light emitted by excitation light source 2 is not limited to laser light, and may be light in other forms (for example, light emitted from a light-emitting diode (LED)) as long as it excites the phosphor.

First light transmitter 3 is a light-transmissive, plate-shaped component, and is approximately orthogonal to the optical axis of excitation light source 2. First light transmitter 3 includes first light-transmissive substrate 31 and dichroic mirror 32.

First light-transmissive substrate 31 is a light-transmissive substrate, and is a component such as sapphire, for example. Dichroic mirror 32 is disposed on the surface of first light-transmissive substrate 31 closer to fluorescent light part 4.

First light transmitter 3 has first entrance surface 3a and first exit surface 3b.

First entrance surface 3a is the surface of first light-transmissive substrate 31 closer to excitation light source 2. First entrance surface 3a has anti-reflective (AR) coat 33 applied thereto. First exit surface 3b is the surface of first light transmitter 3 (the surface closer to second light transmitter 5) opposite the surface on the light entrance side (the side from which the excitation light from excitation light source 2 enters), and is the surface of dichroic mirror 32 closer to fluorescent light part 4.

Fluorescent light part 4 is disposed in close contact with first exit surface 3b of first light transmitter 3 so that the optical axis of excitation light source 2 passes through fluorescent light part 4. Fluorescent light part 4 is a wavelength converter that converts the excitation light passing through first light transmitter 3 and dichroic mirror 32 into predetermined light, and includes a phosphor that emits fluorescent light when irradiated with the excitation light. The phosphor is, for example, an yttrium aluminum garnet (YAG) phosphor or a $BaMgAl_{10}O_{17}$ (BAM) phosphor, and can be selected as appropriate according to the type of the excitation light of excitation light source 2. Further, the phosphor may be, for example, a red phosphor, a green phosphor, or a blue phosphor, and may emit, for example, red, green, or blue fluorescent light when irradiated with the excitation light. Note that although the phosphor in the present embodiment is provided in a portion of first exit surface 3b of first light transmitter 3, the phosphor may be provided over the entire surface of first exit surface 3b.

Note that fluorescent light part 4 may include plural types of phosphors that absorb a portion of blue laser light from excitation light source 2 and emit green to yellow fluorescent light. For example, when blue laser light is emitted from excitation light source 2, a portion of the blue laser light is absorbed by fluorescent light part 4, thereby being converted into green to yellow fluorescent light. The other portion of the blue laser light which has not been absorbed by the phosphor but has passed through the phosphor is combined with the green to yellow fluorescent light. As a result, fluorescent light part 4 emits pseudo white illumination light.

Fluorescent light part 4 is formed by dispersing particulates of a predetermined phosphor in a binder that is a transparent material made from, for example, ceramics or a silicone resin. That is to say, the binder is a medium that binds the phosphor in fluorescent light part 4. The binder included in fluorescent light part 4 is not limited to ceramics or a silicone resin; other transparent materials such as transparent glass may be used.

Second light transmitter 5 is disposed on the side of fluorescent light part 4 closer to light transmission fiber 13 so that fluorescent light part 4 is interposed between first light transmitter 3 and second light transmitter 5. Second light transmitter 5 is a light-transmissive, plate-shaped component, and is disposed across fluorescent light part 4 from first light transmitter 3. Second light transmitter 5 includes second light-transmissive substrate 51 and microfabricated film 52 (an example of a light collecting structure).

Second light-transmissive substrate 51 is a light-transmissive substrate, and is a component such as sapphire, for example. Microfabricated film 52 is disposed on the surface of second light-transmissive substrate 51 opposite the surface closer to fluorescent light part 4.

Second light transmitter 5 has second entrance surface 5a and second exit surface 5b.

Second entrance surface 5a is the surface of second light-transmissive substrate 51 closer to fluorescent light part 4, and is a surface through which light passing through fluorescent light part 4 enters and which is approximately perpendicular to the optical axis of excitation light source 2. In the present embodiment, when optical device 1 is viewed in the optical axis direction, second entrance surface 5a overlaps fluorescent light part 4. A gap between second light transmitter 5 and fluorescent light part 4 is filled with transparent body 91. In other words, since transparent body 91 is provided to fill the gap between fluorescent light part 4 and second light transmitter 5, the air, for example, is absent between second light transmitter 5 and fluorescent light part 4. To put it differently, second light transmitter 5 is in close contact with fluorescent light part 4 via transparent body 91. Transparent body 91 is a light-transmissive silicone resin, for example.

Second exit surface 5b is the surface of second light transmitter 5 closer to light transmission fiber 13, and is a surface through which the light from fluorescent light part 4 (the excitation light and the fluorescent light which have entered through second entrance surface 5a) exits and which is approximately perpendicular to the optical axis of excitation light source 2. In the present embodiment, when optical device 1 is viewed in the optical axis direction, second exit surface 5b overlaps fluorescent light part 4 and second entrance surface 5a.

Microfabricated film 52 is a film having a micro-optical structure. Microfabricated film 52 has a plurality of protrusions 53 that collect, toward light transmission fiber 13, the light passing through second light-transmissive substrate 51. The plurality of protrusions 53 are arranged in a matrix on second exit surface 5b of second light transmitter 5. In the present embodiment, each protrusion 53 is a quadrangular pyramid. Microfabricated film 52 has an approximately isosceles triangular cross section when cut along the plane specified by the X axis direction and the Z axis direction relative to second exit surface 5b (the plane approximately perpendicular to second exit surface 5b). Second exit surface 5b is the surface of microfabricated film 52 closer to light transmission fiber 13. In the present embodiment, light collection encompasses light collimation.

Note that although microfabricated film 52 is a film having this structure, it is not limited to such a film, and may be a structure formed on second exit surface 5b of second light transmitter 5. In this case, the microfabricated film is unnecessary. Furthermore, in the present embodiment, transparent body 92 is disposed also between microfabricated film 52 and second light-transmissive substrate 51. Transparent body 92 is also a light-transmissive silicone resin, for example.

Figure 4:
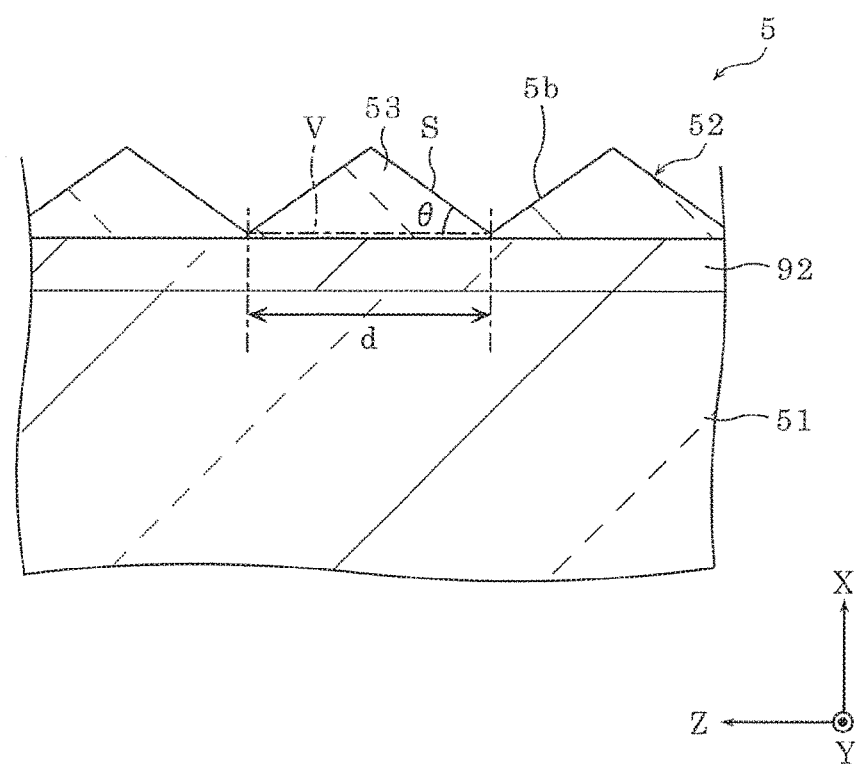
FIG. 4 is a partially enlarged schematic cross sectional view illustrating the second light transmitter of the optical device according to the embodiment.

Microfabricated film 52 will be described with reference to FIG. 4 illustrating its cross section.

FIG. 4 is a partially enlarged schematic cross sectional view illustrating second light transmitter 5 of optical device 1 according to the present embodiment.

As illustrated in FIG. 4, virtual undersurface V and inclined surface S form angle θ of at least 30° and at most 65°. Each protrusion 53 has virtual undersurface V on the side closer to second light transmitter 5 and four inclined surfaces S apart from virtual undersurface V. That is to say, the length of virtual undersurface V is width (pitch) d of protrusion 53.

Figure 5:
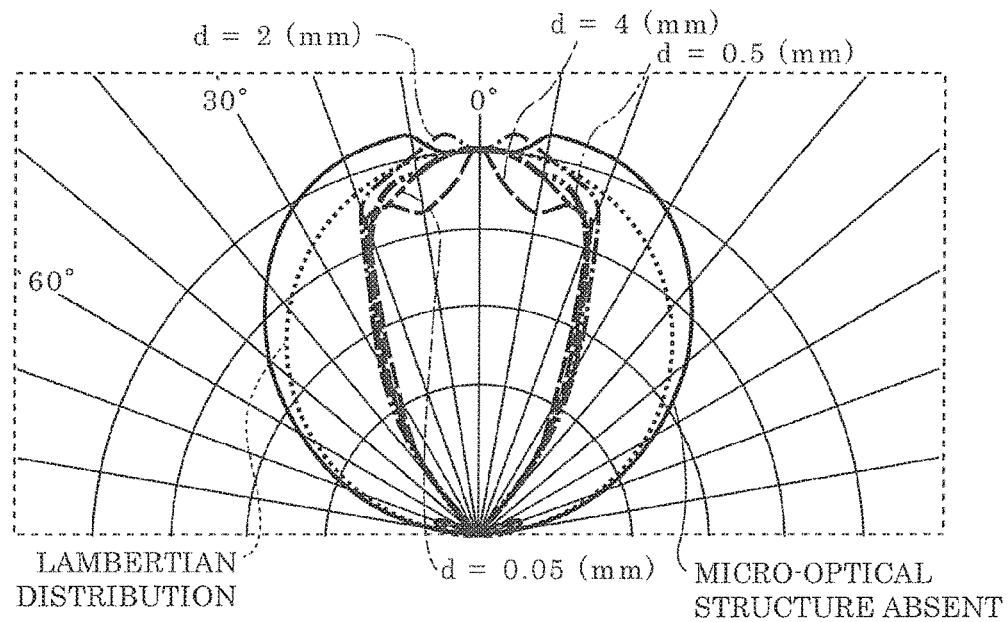
FIG. 5 illustrates distribution of light exiting through a second exit surface of the optical device according to the embodiment.
Figure 6:
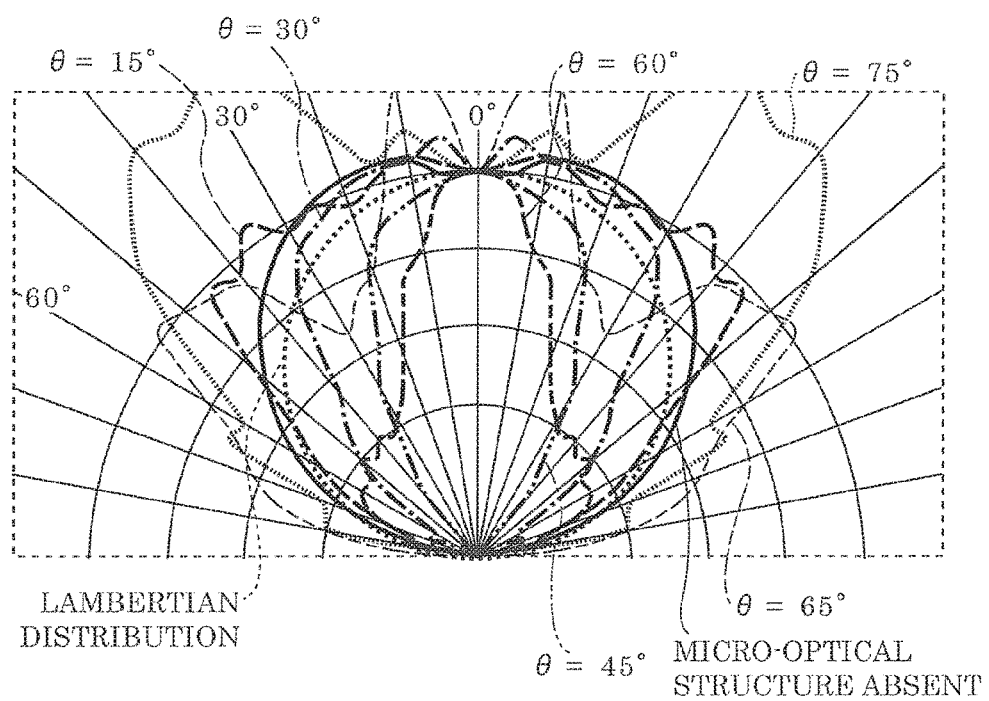
FIG. 6 illustrates distribution of light exiting through the second exit surface of the optical device according to the embodiment.

With reference to FIG. 5 and FIG. 6, results of simulations of light distribution of optical device 1 that includes such microfabricated film 52 will be described.

FIG. 5 illustrates distribution of light exiting through second exit surface 5b of optical device 1 according to the present embodiment. FIG. 6 illustrates distribution of light exiting through second exit surface 5b of optical device 1 according to the present embodiment.

Sapphire is used as second light transmitter 5 in these simulations. The thickness of the sapphire excluding microfabricated film 52 is 0.5 mm, angle θ is 45°, the refractive index of the sapphire is 1.77, and the size of excitation light source 2 is 2 mmφ. The surrounding area of first light transmitter 3 and second light transmitter 5 is filled with the air.

FIG. 5 illustrates light distribution in the following cases: microfabricated film 52 is absent; width d of protrusion 53=4 mm; width d of protrusion 53=2 mm; width d of protrusion 53=0.5 mm; and width d of protrusion 53=0.05 mm. 0° indicates the optical axis direction (light emission direction). FIG. 5 also illustrates the case of Lambertian distribution as a standard for ideal diffuse reflection.

Although the light distribution is somewhat uneven in the optical axis direction when width d of protrusion 53 is 2 mm and when width d of protrusion 53 is 4 mm, there is no significant change to the light distribution even when width d of protrusion 53 changes. That is to say, the impact that width d of protrusion 53 has on the light distribution can be considered to be small. Furthermore, it was found that when width d of protrusion 53 is 2 mm, the directivity decreases because width d approaches the size of excitation light source 2.

Next, a simulation was performed by fixing width d of protrusion 53 at 0.5 mm and changing angle θ. The other settings of optical device 1 were kept the same.

FIG. 6 illustrates light distribution in the following cases: microfabricated film 52 is absent; angle θ=15°; angle θ=30°; angle θ=45°; angle θ=60°; angle θ=65°; and angle θ=75°.

The result was that: the unevenness in the light distribution decreased as angle θ increased from 15°; the shape of the light distribution became an approximate ellipse when angle θ was 45° and when angle θ was 60°; and the light distribution became uneven again as the angle further increased. This result has shown that the light distribution significantly changes depending on angle θ. That is to say, the directivity of the light is considered to have a peak, i.e., become highest, when angle θ is in the vicinity of 60°. The range of angle θ was determined based on the above results.

As illustrated in FIG. 3, light transmission fiber 13 is a light-transmissive optical fiber that has third entrance surface 13a and guides the light exiting from second light transmitter 5. Third entrance surface 13a is a surface on one end side of light transmission fiber 13. The light exiting from second light transmitter 5 enters light transmission fiber 13 through third entrance surface 13a with third entrance surface 13a separated from second exit surface 5b of second light transmitter 5. In other words, third entrance surface 13a is approximately perpendicular to the optical axis of excitation light source 2. The other end portion of light transmission fiber 13 is connected to tip end portion 15.

In the present embodiment, when optical device 1 is viewed in the optical axis direction, third entrance surface 13a overlaps fluorescent light part 4, second entrance surface 5a, and second exit surface 5b. That is to say, excitation light source 2, first light transmitter 3, fluorescent light part 4, second light transmitter 5, and light transmission fiber 13 are arranged in this order. Note that fluorescent light part 4, second entrance surface 5a, second exit surface 5b, and third entrance surface 13a of light transmission fiber 13 are the same in size in the present embodiment; however, their sizes may be different and changeable as necessary.

Light source controller 6 controls, via power source 7, an operation of excitation light source 2 such as light emission, and includes, for instance, a circuit for controlling excitation light source 2, for example. Light source controller 6 achieves its operation using a microcomputer, a processor, etc., or a dedicated circuit that controls, for example, current supplied to excitation light source 2.

Power source 7 includes a power source circuit that generates power for causing excitation light source 2 to emit light. Power source 7 is electrically connected to a power system by a power line such as a control line.

Camera control unit 12 controls tip end portion 15. Camera control unit 12, for example, is accommodated in a housing.

The other end portion of light transmission fiber 13 and the other end portion of image transmission path 14 are connected to tip end portion 15. Tip end portion 15 includes camera 16 that captures an image of an object. Camera 16 is a charge-coupled device (CCD) camera, for example. Camera 16 transmits a signal of the captured image of the object to image processor 12a of camera control unit 12 via image transmission path 14. Image processor 12a performs appropriate image processing by converting the input signal of the image into image data, so as to generate output image information desired. The image information generated is then displayed on a display via controller 12b as an observation image of the endoscope. Further, the image information is recorded as necessary on recorder 12c that includes memory, for example.

With such optical device 1, the excitation light emitted from excitation light source 2 enters and passes through first light transmitter 3 and then enters fluorescent light part 4. A portion of the excitation light entering fluorescent light part 4 is absorbed by the phosphor and emitted as fluorescent light, whereas another portion of the excitation light entering fluorescent light part 4 passes through fluorescent light part 4 as it is. The fluorescent light and excitation light pass through second light transmitter 5, exit through second exit surface 5b, and enter third entrance surface 13a of light transmission fiber 13. The fluorescent light and excitation light then pass through light transmission fiber 13, reach tip end portion 15, and exit from tip end portion 15.

Advantageous Effects

Next, advantageous effects of optical device 1 according to the present embodiment will be described.

As described above, optical device 1 according to the present embodiment includes: excitation light source 2; first light transmitter 3 that transmits excitation light emitted from excitation light source 2; fluorescent light part 4 that is disposed on a surface of first light transmitter 3 opposite a surface through which the excitation light enters, and emits fluorescent light from the excitation light; second light transmitter 5 that interposes fluorescent light part 4 with first light transmitter 3, and transmits light emitted from fluorescent light part 4; light transmission fiber 13 that guides the light exiting from second light transmitter 5; and microfabricated film 52 that is disposed on a side of second light transmitter 5 closer to light transmission fiber 13, and collects, toward light transmission fiber 13, the light emitted from fluorescent light part 4.

According to this configuration, since fluorescent light part 4 is interposed between first light transmitter 3 and second light transmitter 5, heat from fluorescent light part 4 can be more easily dissipated as compared the case where fluorescent light part 4 is in contact with first light transmitter 3 only.

Furthermore, with optical device 1, the distance between fluorescent light part 4 and light transmission fiber 13 is greater than that in an optical device which does not include second light transmitter 5, by the thickness of second light transmitter 5. However, since microfabricated film 52 is disposed on the side of second light transmitter 5 closer to light transmission fiber 13, light passing through second light transmitter 5 is collected by microfabricated film 52 and easily enters third entrance surface 13a of light transmission fiber 13.

Therefore, optical device 1 can enhance the dissipation of heat from fluorescent light part 4 and the light collection toward light transmission fiber 13. This makes it possible to increase the density of light bundles guided by light transmission fiber 13.

Further, in optical device 1 according to the present embodiment, a gap between fluorescent light part 4 and second light transmitter 5 is filled with transparent body 91.

According to this configuration, since the gap between fluorescent light part 4 and second light transmitter 5 is bridged by (filled with) transparent body 91, it is possible to reduce Fresnel loss where light entering second light transmitter 5 is reflected by second entrance surface 5a of second light transmitter 5, and to increase the dissipation of heat from fluorescent light part 4. As a result, it is possible to increase the light extraction efficiency in second light transmitter 5.

Further, in optical device 1 according to the present embodiment, transparent body 91 has a refractive index greater than or equal to a refractive index of a binder that binds a phosphor in fluorescent light part 4.

According to this configuration, since the light emitted from fluorescent light part 4 is further refracted by transparent body 91 toward the optical axis, the light easily travels toward the optical axis. Thus, light exiting from second light transmitter 5 is less likely to be diffused. As a result, it is possible to increase the light extraction efficiency in light transmission fiber 13.

Further, in optical device 1 according to the present embodiment, microfabricated film 52 includes a plurality of protrusions 53. The plurality of protrusions 53 are each a quadrangular pyramid and are arranged in a matrix on a surface of second light transmitter 5 closer to light transmission fiber 13.

According to this configuration, the fluorescent light passing through second light transmitter 5 is refracted by second exit surface 5b of microfabricated film 52 and is easily collected by microfabricated film 52 (collimated light is easily included). As a result, highly directional light exits through second exit surface 5b.

Further, in optical device 1 according to the present embodiment, each of the plurality of protrusions 53 has virtual undersurface V on a side closer to second light transmitter 5 and four inclined surfaces S. Virtual undersurface V and each inclined surface S form an angle $\theta$ of at least 30° and at most 65°.

According to this configuration, as illustrated in FIG. 5 and FIG. 6, appropriately setting angle $\theta$ enables obtaining light collected by second light transmitter 5. As a result, more highly directional light exits through second exit surface 5b.

Further, in optical device 1 according to the present embodiment, width d of each of the plurality of protrusions 53 is at least 0.01 mm and at most 3 mm.

As in this configuration, width d of protrusion 53 makes the thickness of microfabricated film 52 not easily increase due to the relationship with angle $\theta$, and thus the thickness of second light transmitter 5 does not easily increase. For this reason, the distance between fluorescent light part 4 and light transmission fiber 13 is not easily influenced, and the light collected by second exit surface 5b exits from microfabricated film 52.

In particular, even when width d of protrusion 53 is changed, since width d does not depend on the light wavelength, light can be collected without adjusting the light wavelength.

(Variation of Embodiment)

Hereinafter, optical device 1 according to a variation of the present embodiment will be described with reference to FIG. 7.

Figure 7:
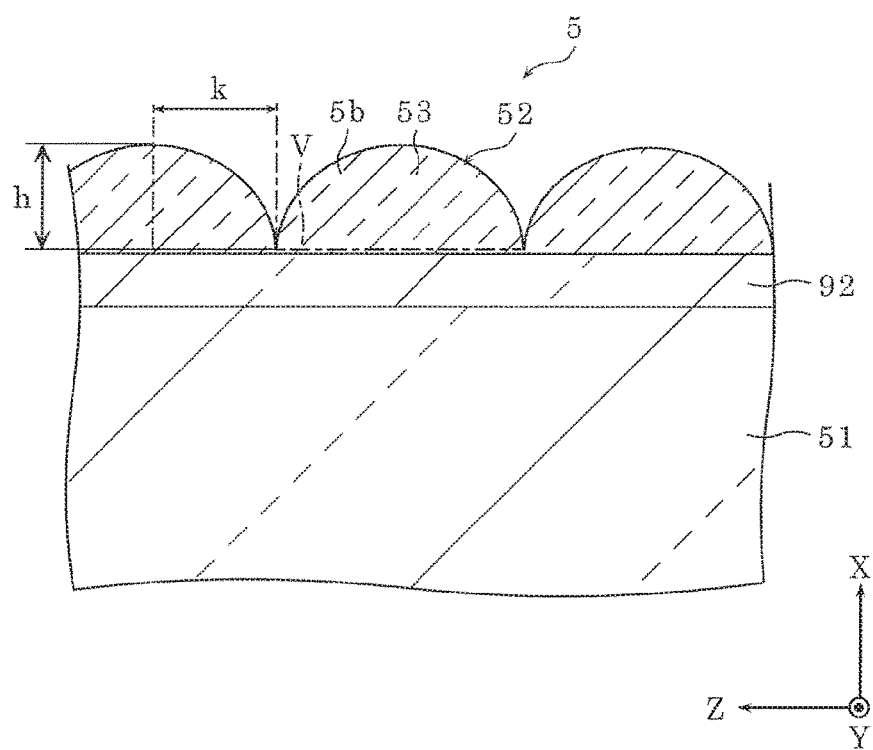
FIG. 7 is a partially enlarged schematic cross sectional view illustrating a second light transmitter of an optical device according to a variation of the embodiment.

FIG. 7 is a partially enlarged schematic cross sectional view illustrating second light transmitter 5 of optical device 1 according to the variation of the present embodiment.

The variation of the above embodiment is different from the above embodiment in that while protrusions 53 of microfabricated film 52 in the above embodiment are quadrangular pyramids, protrusions 53 of microfabricated film 52 in the variation of the embodiment are approximately semispherical.

The other elements in the variation are the same as those of the above embodiment; identical reference signs are given to identical elements, and detailed descriptions of such elements will be omitted.

The plurality of protrusions 53 each form a portion of an approximate spherical body and are arranged in a matrix on second exit surface 5*b* of microfabricated film 52 in second light transmitter 5. Note that protrusions 53 in the variation of the present embodiment are approximately semispherical of the present embodiment are approximately semispherical.

When k represents a half width (½ pitch) that is half the width of each virtual undersurface V, and h represents the height of each of the plurality of protrusions 53 in the direction of the optical axis of excitation light source 2, the plurality of protrusions 53 of microfabricated film 52 satisfy the condition of.

[Math. 1]

$$\frac{h}{k} \geq 0.5 \qquad \text{Expression 1}$$

A half the width of virtual undersurface V, referred to as half width k, is the width of protrusion 53. In other words, half width k of virtual undersurface V is the radius of the circular virtual undersurface. Half width k of each virtual undersurface V is at least 0.01 mm and at most 3 mm. Height h in the direction of the optical axis of excitation light source 2 is at least 0.01 mm and at most 3 mm. h/k represents the aspect ratio. Height h of protrusion 53 in the direction of the optical axis of excitation light source 2 represents the height from virtual undersurface V.

Figure 8:
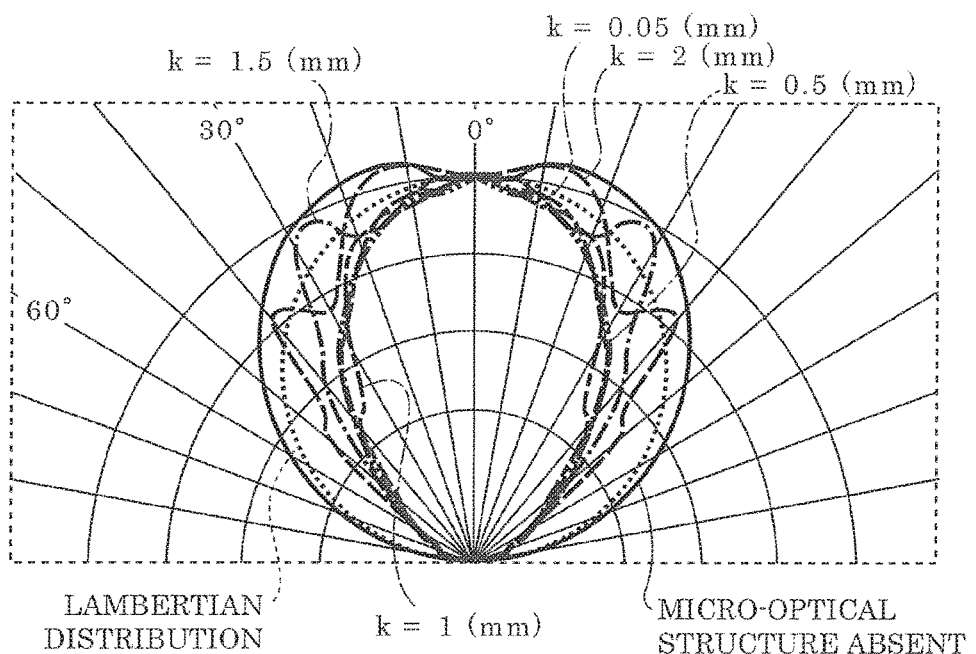
FIG. 8 illustrates distribution of light exiting through a second exit surface of the optical device according to the variation of the embodiment.
Figure 9:
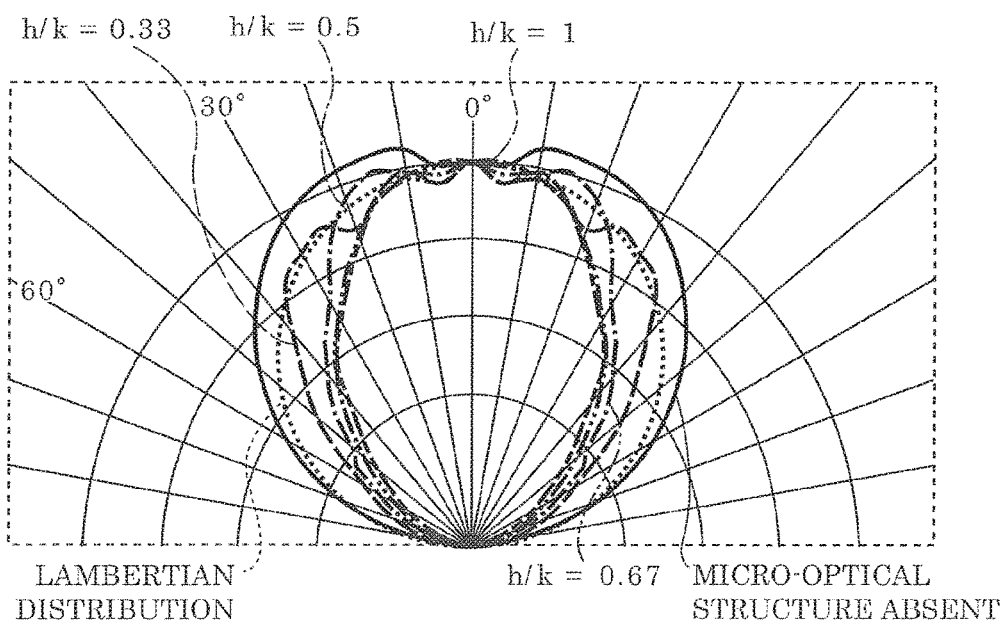
FIG. 9 illustrates distribution of light exiting through the second exit surface of the optical device according to the variation of the embodiment.

With reference to FIG. 8 and FIG. 9, results of simulations of light distribution of optical device 1 that includes such microfabricated film 52 will be described.

FIG. 8 illustrates distribution of light exiting through second exit surface 5*b* of optical device 1 according to the variation of the present embodiment. FIG. 9 illustrates distribution of light exiting through second exit surface 5*b* of optical device 1 according to the variation of the present embodiment.

FIG. 8 illustrates light distribution in the following cases: microfabricated film 52 is absent; half width k of virtual undersurface V=2 mm; half width k of virtual undersurface V=1.5 mm; half width k of virtual undersurface V=1 mm; half width k of virtual undersurface V=0.5 mm; and half width k of virtual undersurface V=0.05 mm.

While the light distribution is approximately elliptical in the cases where half width k of virtual undersurface V is 0.05 mm, 0.5 mm, and 1 mm, it can be seen that light distribution is uneven in the cases where half width k of virtual undersurface V is 1.5 mm and 2 mm. That is to say, half width k of virtual undersurface V can be considered to have a property that easily influences the light distribution as compared to protrusions 53 of the embodiment.

FIG. 9 illustrates light distribution in the following cases: microfabricated film 52 is absent; aspect ratio h/k=0.33; aspect ratio h/k=0.5; aspect ratio h/k=0.67; and aspect ratio h/k=1.

The result was that the light distribution was approximately elliptical when aspect ratio h/k was 0.5, 0.67, and 1, and the light distribution was uneven when aspect ratio h/k was 0.33. That is to say, the result was that the light distribution became uneven as aspect ratio h/k decreased, and the light became more directional as aspect ratio h/k increased. Aspect ratio h/k in Expression 1 was determined based on the above result.

Advantageous Effects

Next, advantageous effects of optical device 1 according to the variation of the present embodiment will be described.

As described earlier, microfabricated film 52 of optical device 1 according to the variation of the present embodiment includes a plurality of protrusions 53. The plurality of protrusions 53 each form a portion of an approximate spherical body and are arranged in a matrix on a surface of second light transmitter 5 closer to light transmission fiber 13.

According to this configuration, the light passing through second light transmitter 5 is refracted by second exit surface 5*b* of microfabricated film 52 and is easily collected by microfabricated film 52. As a result, highly directional light exits through second exit surface 5*b*.

Further, in optical device 1 according to the present embodiment, each of the plurality of protrusions 53 has virtual undersurface V on a side closer to second light transmitter 5. When k represents a half width that is half the width of virtual undersurface V, and h represents the height of each of the plurality of protrusions 53 in the direction of the optical axis of excitation light source 2, microfabricated film 52 satisfies the condition of:

[Math. 2]

$$\frac{h}{k} \geq 0.5 \qquad \text{Expression 2}$$

According to this configuration, as illustrated in FIG. 8 and FIG. 9, light can be collected by second light transmitter 5 when the condition of Expression 2 is satisfied. For this reason, more highly directional light exits through second exit surface 5*b*.

Further, in optical device 1 according to the present embodiment, height h of each of the plurality of protrusions 53 in the direction of the optical axis of excitation light source 2 is at least 0.01 mm and at most 3 mm.

As in this configuration, height h of protrusion 53 makes the height of microfabricated film 52 not easily increase, and thus the thickness of second light transmitter 5 does not easily increase. For this reason, the distance between fluorescent light part 4 and light transmission fiber 13 is not easily influenced, and the light collected by second exit surface 5*b* exits from microfabricated film 52.

In particular, even when width d of protrusion 53 is changed, since width d does not depend on the light wavelength, light can be collected without adjusting the light wavelength.

The other advantageous effects of optical device 1 according to the variation of the present embodiment are the same as those produced by optical device 1 according to the present embodiment.

(Other Variations Etc.)

Hereinbefore, the optical device according to the present disclosure has been described based on an embodiment and a variation of the embodiment; however, the present disclosure is not limited to the above embodiment and variation of the embodiment.

For example, the protrusions of the light collecting structure in the above embodiment and variation of the embodiment may be triangular pyramids, cubes etc., or a shape combining these shapes.

Furthermore, the phosphor in the above embodiment and variation of the embodiment may be, for example, various powder phosphors, ceramic phosphors, or monocrystal phosphors.

Hereinbefore, one or more aspects of the present disclosure have been described based on an embodiment and a variation of the embodiment; however, the present disclosure is not limited to this embodiment and the variation of this embodiment. Various modifications to this embodiment and the variation of this embodiment conceived by those skilled in the art, as well as embodiments resulting from combinations of structural elements of different embodiments may be included within the scope of one or more aspects of the present disclosures as long as such modifications and embodiments do not depart from the essence of the present disclosure.

While the foregoing has described one or more embodiments and/or other examples, it is understood that various modifications may be made therein and that the subject matter disclosed herein may be implemented in various forms and examples, and that they may be applied in numerous applications, only some of which have been described herein. It is intended by the following claims to claim any and all modifications and variations that fall within the true scope of the present teachings.

What is claimed is:

1. An optical device, comprising:
   an excitation light source;
   a first light transmitter that transmits excitation light emitted from the excitation light source;
   a fluorescent light part that is disposed on a surface of the first light transmitter opposite a surface through which the excitation light enters, and emits fluorescent light from the excitation light;
   a second light transmitter that interposes the fluorescent light part with the first light transmitter, and transmits light emitted from the fluorescent light part;
   a light guide that guides the light exiting from the second light transmitter, and
   a light collecting structure including a plurality of protrusions and that is disposed on a side of the second light transmitter closer to the light guide, and collects, toward the light guide, the light emitted from the fluorescent light part, wherein:
   the plurality of protrusions each form a portion of an approximate spherical body and are arranged in a matrix on a surface of the second light transmitter closer to the light guide,
   each of the plurality of protrusions has a virtual undersurface on a side closer to the second light transmitter, and
   when k represents a half width that is half a width of the virtual undersurface, and h represents a height of each of the plurality of protrusions in a direction of an optical axis of the excitation light source, the light collecting structure satisfies a condition of:

[Math. 1]

$$\frac{h}{k} \geq 0.5. \qquad \text{Expression 1}$$

2. The optical device according to claim 1, wherein the height h of each of the plurality of protrusions in the direction of the optical axis of the excitation light source is at least 0.01 mm and at most 3 mm.

3. The optical device according to claim 1, wherein an anti-reflective (AR) coat is applied to a first entrance surface of the first light transmitter closer to the excitation light source.

4. The optical device according to claim 1, wherein a dichroic mirror is disposed on the surface of the first light transmitter closer to the fluorescent light part.

5. The optical device according to claim 1, wherein the light emitted from the fluorescent light part is white.

* * * * *